United States Patent
Luther et al.

(10) Patent No.: US 6,521,217 B1
(45) Date of Patent: Feb. 18, 2003

(54) SUN SCREEN FORMULATIONS

(75) Inventors: Helmut Luther, Grenzach-Wyhlen (DE); Albert Stehlin, Rosenau (FR)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/719,905

(22) PCT Filed: Jun. 10, 1999

(86) PCT No.: PCT/EP99/04008

§ 371 (c)(1),
(2), (4) Date: Dec. 20, 2000

(87) PCT Pub. No.: WO99/66896

PCT Pub. Date: Dec. 29, 1999

(30) Foreign Application Priority Data

Jun. 22, 1998 (EP) .............................. 98810571

(51) Int. Cl.⁷ ............................ A61K 7/42; A61K 7/44; A61K 7/00; A61K 31/53
(52) U.S. Cl. ........................ 424/59; 424/60; 424/400; 424/401; 514/241
(58) Field of Search ........................ 424/59, 60, 400, 424/401; 514/241

(56) References Cited

U.S. PATENT DOCUMENTS 5,733,531 A * 3/1998 Mitchnick et al. ............ 424/59

FOREIGN PATENT DOCUMENTS

| | | | |
|---|---|---|---|
| FR | 2696345 | | 4/1994 |
| GB | 2303549 | * | 2/1997 |

OTHER PUBLICATIONS

Electronic version of Ullmann's Encyclopedia of Industrial Chemistry, "Alkyl Polyglucosides".

* cited by examiner

*Primary Examiner*—Shelley A. Dodson
(74) *Attorney, Agent, or Firm*—Kevin T. Mansfield

(57) ABSTRACT

Disclosed is sun screen formulation, comprising (a) a micronised organic UV absorber, and (b) a cosmetically acceptable carrier, wherein the micronised organic UV absorber is present in the oil phase of the formulation. The sunscreen composition of the invention provides excellent protection of the human skin against the damaging effects of sunlight, while permitting safe tanning of the skin.

23 Claims, No Drawings

SUN SCREEN FORMULATIONS

The present invention relates to new formulations and, in particular, to new UV-protection formulations which comprise a micronised UV absorber, wherein the micronised UV absorber is present in the oil phase of the formulation.

It has long been known that prolonged exposure to UV radiation which reaches the surface of the earth can lead to the formation of erythemas or light dermatoses, as well as to an increased incidence of skin cancers, or accelerated skin ageing.

Various sunscreen formulations have been proposed which include a material which is intended to counteract UV radiation, thereby inhibiting the said undesired effects on the skin.

A great number of compounds has been proposed for use as UV protectants in sunscreen formulations, especially soluble organic UV absorbers and insoluble micronised inorganic compounds, in particular zinc oxide and titanium dioxide.

With respect to the use in sunscreen formulations of soluble organic UV absorbers, they have the disadvantages that their effectiveness as UV protectants in terms of SPF (Sun Protection Factor) in a sunscreen formulation is often too low for commercial purposes; as a result of their solubility, they exhibit relatively high allergenic potential; and that as a result of intrinsic photochemical lability, the duration of the protective effect is often too low.

The high specific weight of insoluble inorganic compounds, such as titanium dioxide leads to a reduced stability of formulations containing them. Moreover, such inorganic compounds have been claimed to generate toxic radicals under the influence of light and water ("Redox Mechanisms in Heterogeneous Photocatalysis", Serpone et al, Electrochemistry in Colloids and Dispersions, Editors Mackay and Texter, VCH Publishers Inc., NewYork 1992).

In GB-A-2303549, there is described a method of producing micronised, insoluble organic UV absorbers, as well as a sunscreen composition comprising a) 0.1 to 15%, preferably 0.5 to 10% by weight, based on the total composition of a micronised formulation of an insoluble organic UV absorber, produced according to the said method; and optionally b) a cosmetically acceptable carrier.

Micronised, insoluble organic UV absorbers so obtained, when used in sunscreen formulations, provide excellent UV protection and have at least as high an SPF rating as corresponding sunscreen formulations containing a known inorganic UV absorber. Unlike the latter UV absorbers, micronised, insoluble organic UV absorbers show no tendency, under the influence of light, to generate radicals which could damage or sensitise human skin.

In a further development of the concept disclosed in GB-A-2303549, it has now been found that, micronised, insoluble organic UV absorbers which are present in the oil phase of the sun screen formulation surprisingly show a significant improvement in sun protection.

Accordingly, the present invention provides, as a first aspect, a sun screen formulation, which is especially suitable for use in pharmaceutical or cosmetic applications, comprising (a) a micronised organic UV absorber; and (b) a cosmetically acceptable carrier, wherein the micronised organic UV absorber is present in the oil phase of the formulation.

The micronised organic UV absorber, component (a), is preferably produced by the method described in GB-A-2303549, namely by a process which comprises grinding an organic UV absorber, in coarse particle form, in a grinding apparatus, in the presence of 1 to 50%, preferably 5 to 40% by weight, based on the micronised organic UV absorber, of an alkyl polyglucoside having the formula $C_nH_{2n+1}O(C_6H_{10}O_5)_xH$, in which n is an integer ranging from 8 to 16 and x is the mean polymerisation level of the glucoside moiety $(C_6H_{10}O_5)$ and ranges from 1.4 to 1.6, or an ester thereof.

The grinding apparatus used to produce the micronised organic UV absorber may be, e.g., a jet, ball, vibration or hammer mill, preferably a high speed stirring mill or impact mill, especially a rotating ball mill, vibrating mill, tube mill or rod mill.

The alkyl polyglucoside may consist of a $C_1$–$C_{12}$ester of the compound of formula $C_nH_{2n+1}O(C_6H_{10}O_5)_xH$, namely an ester formed by reacting a $C_1$–$C_{12}$acid, such formic, acetic, propionic, butyric, sulfosuccinic, citric or tartaric acid, with one or more free OH groups on the glucoside moiety $(C_6H_{10}O_5)$.

The micronised organic UV absorber may be incorporated into the oil phase with different methods.

In a preferred incorporation method the micronised organic UV absorber may be incorporated as powder. For this purpose the micronised organic UV absorber may be subjected to known powdering processes like solvent precipitation, vacuum spraying from solvents etc. These powders have a particle size of 0, 1 nm to 2 $\mu$m. In order to prevent agglomeration processes the micronised organic UV absorber may be coated before powdering with a surface active agent like nonionic, anionic, cationic or amphoteric surfactants like phospholipids or known polymers, for example PVP, acrylates etc.

As example, a water-soluble surfactant or emulsifier is added to the aqueous suspension of the micronised organic UV absorber. The mixture is then spray-dried. During the spray-drying process the surfactant or emulsifier sheathes the micro-particles in form of a thin film and inhibits aggregation or facilitates the re-dispersion to the desired particle size in the oil phase.

In another preferred method the micronised organic UV absorber may be transferred to the oil phase during the preparation of the sun screen formulation: when mixing the micronised organic UV absorber which was produced by aqueous grinding with the oil phase of the sun screen formulation the water will be removed by known methods like vacuum removal. By this measure the micronised organic UV absorber will be transferred to the oil phase of the formulation.

Furthermore, it was observed that the micronised organic UV absorber which is present in the aqueous phase of the sun screen composition will migrate into the oil phase after a couple of days or weeks.

Therefore, another aspect the present invention refers to a method of preparation of the sunscreen composition by micronising the organic UV absorber in the first step as aqueous suspension, mixing the micronised organic UV absorber with the oil phase of the sunscreen composition in a second step and storing the formulation for at least three weeks in a final step.

Suitable organic UV absorber may be, e.g., a triazine, a benzotriazole, a vinyl group-containing amide, a cinnamic acid amide or a sulfonated benzimidazole UV absorber.

A preferred class of triazine compounds is that having the formula

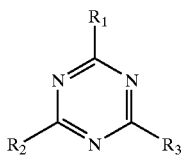
(1)

in which

R₁, R₂ and R₃, independently, are H; OH; $C_1$–$C_3$alkoxy; $NH_2$; NH—$R_4$; N($R_4$)₂; $OR_4$, wherein $R_4$ is $C_1$–$C_3$ alkyl; phenyl; phenoxy; anilino; pyrrolo, in which the respective phenyl, phenoxy or anilino, or pyrrolo moieties are not substituted or substituted by one, two or three substitutents selected from OH, carboxy, CO—$NH_2$, $C_1$–$C_3$alkyl, $C_1$–$C_3$alkoxy, a methylidenecamphor group, a group —(CH=CH)$_m$C(=O)—$OR_4$, a group

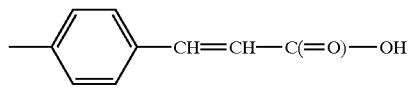

or the corresponding alkali metal, ammonium, mono-, di- or tri-$C_1$–$C_4$alkylammonium, mono-, di- or tri-$C_2$–$C_4$alkanolammonium salts, or the $C_1$–$C_3$alkyl esters thereof, a radical of formula (1a)

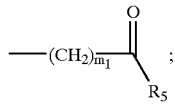
(1a)

$R_5$ is hydroxy; $C_1$–$C_5$alkyl that is unsubstituted or substituted by one or more OH groups; $C_1$–$C_5$alkoxy; amino; mono- or di-$C_1$–$C_5$alkylamino; M; a radical of formula

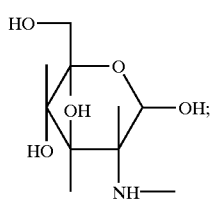
(1b)

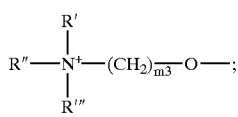
(1c)

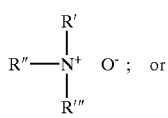
(1d)

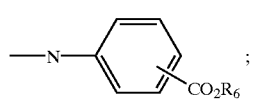
(1e)

R′, R″ and R′″ are each independently of the others $C_1$–$C_{14}$alkyl that is unsubstituted or substituted by one or more OH groups;

$R_6$ is hydrogen; M; $C_1$–$C_5$alkyl; or a radical of the formula —(CH₂)$_{m_2}$—O—$T_1$;

M is a metal cation;

$T_1$ is hydrogen; or $C_1$–$C_8$alkyl;

m is 0 or 1;

$m_1$ is from 1 to 5;

$m_2$ is from 1 to 4;

$m_3$ is from 2 to 14.

Preferred compounds of formula (1) are those having the formula

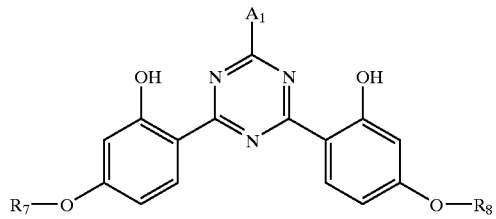
(2)

in which $R_7$ and $R_8$, independently of one another, are $C_1$–$C_{18}$alkyl; $C_2$–$C_{18}$alkenyl; a radical of the formula —CH₂—CH(—OH)—CH₂—O—$T_1$; or; a radical of the formula —(CH₂)$_{\overline{m_1}}$O—((CH₂)$_{\overline{m_2}}$T₂; a radical of the formula

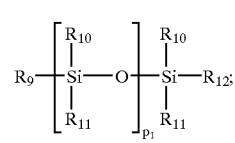
(2a)

$R_9$ is a direct bond; a straight-chain or branched $C_1$–$C_4$alkylene radical or a radical of the formula —$C_{m_1}H_{2m_1}$— or —$C_{m_1}H_{2m_1}O$—;

$R_{10}$, $R_{11}$ and $R_{12}$, independently of one another, are $C_1$–$C_{18}$alkyl; $C_1$–$C_{18}$alkoxy or a radical of the formula

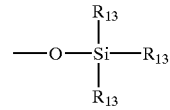

$R_{13}$ is $C_1$–$C_5$alkyl;

$T_1$ is hydrogen; or $C_1$–$C_8$alkyl;

$m_1$, $m_2$ and $m_3$, independently of one another, are 1 to 4;

$p_1$ is 0 or a number from 1 to 5;

$A_1$ is a radical of the formula

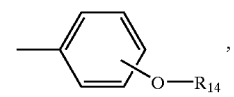
(2b)

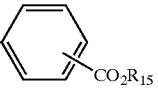
(2c)

or of the formula

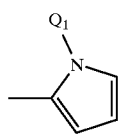  (2d)

$R_{14}$ is hydrogen; $C_1$–$C_{10}$ alkyl, —(CH$_2$CHR$_{16}$—O)$_{n_1}$—R$_{15}$; —CH$_2$—CH(—OH)—CH$_2$—O—T$_1$; or a radical of the formula —(CH$_2$)$_{\overline{m_1}}$O—((CH$_2$)$_{\overline{m_2}}$T$_2$;

$R_{15}$ is hydrogen; M; $C_1$–$C_5$alkyl; or a radical of the formula —(CH$_2$)$_{m_2}$—O—T$_1$;

$R_{16}$ is hydrogen; or methyl;

$Q_1$ $C_1$–$C_{18}$alkyl;

M is a metal cation; and $n_1$ is 1–16.

Preferred compounds of formula (2) are those of formulae

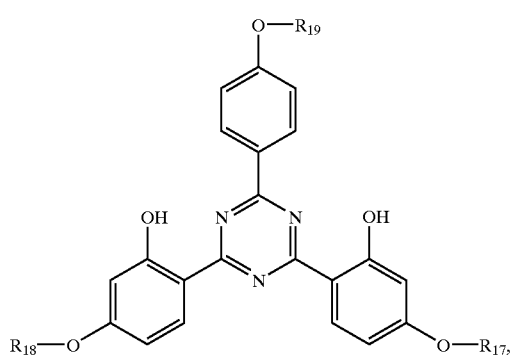  (2e)

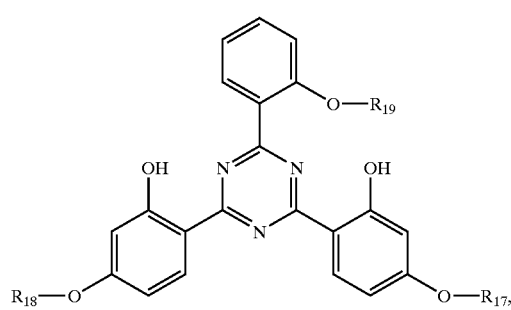  (2f)

the formula

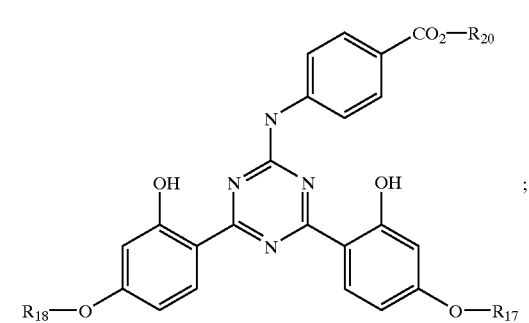  (2g)

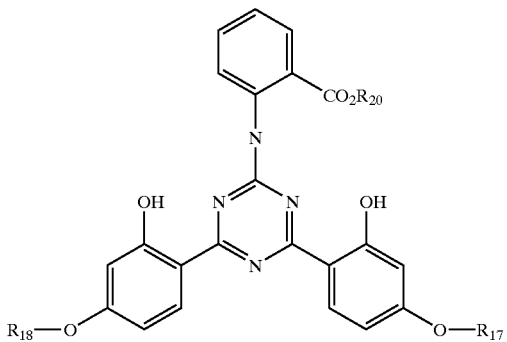  (2h)

in which $R_{17}$ and $R_{18}$, independently of one another, are $C_3$–$C_{18}$alkyl; or —CH$_2$—CH(—OH)—CH$_2$—O—T$_1$;

$R_{19}$ is $C_1$–$C_{10}$alkyl or a radical of the formula

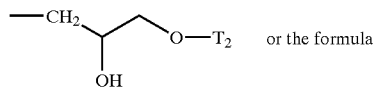  (2a$_1$)

or the formula

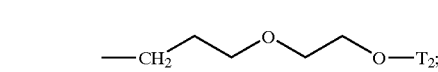  (2a$_2$)

$R_{20}$ is hydrogen; M; $C_1$–$C_5$alkyl; —NH—$C_1$–$C_5$alkyl, preferably —NH-tert.alkyl; or a radical of the formula —(CH$_2$)$_m$—O—T$_2$;

$T_1$ and $T_2$ independently of one another, are hydrogen; or $C_1$–$C_5$alkyl; and m is 1 to 4.

Uppermost of interest are compounds of the formulae (2e) and (2f), in which $R_{17}$ and $R_{18}$, independently of one another, are $C_3$–$C_{18}$alkyl; or —CH$_2$—CH(—OH)—CH$_2$—O—T$_1$;

$R_{19}$ is $C_1$–$C_{10}$alkyl;

and compounds of the formulae (2g) and (2h), in which $R_{17}$ and $R_{18}$, independently of one another, are $C_3$–$C_{18}$alkyl or —CH$_2$—CH(—OH)—CH$_2$—O—T$_1$; and $T_1$ is hydrogen; or $C_1$–$C_5$alkyl.

Very particularly preferred in this case are triazine compounds of the formula (2e)–(2h), in which $R_{17}$ and $R_{18}$ have the same meaning.

Furthermore, interesting triazines correspond to the formula

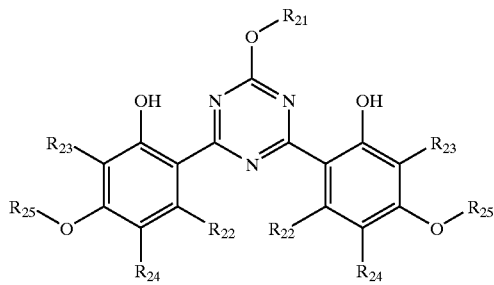
(3)

in which

R$_{21}$ is C$_1$–C$_{30}$alkyl; C$_2$–C$_{30}$alkenyl; unsubstituted or C$_1$–C$_5$alkyl-mono- or polysubstituted C$_5$–C$_{12}$cycloalkyl, C$_1$–C$_5$alkoxy-C$_1$–C$_{12}$alkyl; amino-C$_1$–C$_{12}$alkyl; C$_1$–C$_5$monoalkylamino-C$_1$–C$_{12}$alkyl; C$_1$–C$_5$dialkylamino-C$_1$–C$_{12}$alkyl; a radical of the formula

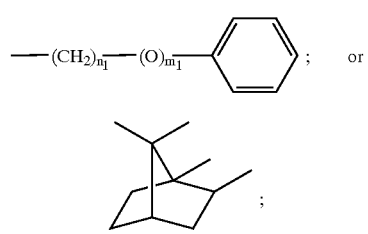
(3a)

(3b)

R$_{22}$, R$_{23}$ and R$_{24}$, independently of one another, are hydrogen, hydroxyl, C$_1$–C$_{30}$alkyl, C$_2$–C$_{30}$alkenyl, R$_{25}$ is hydrogen; or C$_1$–C$_5$alkyl;

m$_1$ is 0 or 1; and n$_1$ is 1 to 5.

Preferred compounds correspond to the formula

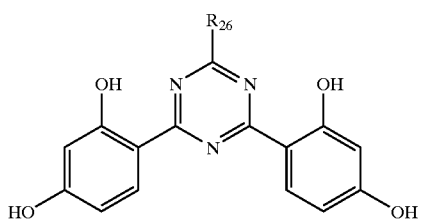
(4)

wherein

R$_{26}$ is —O—CH$_2$—CH(n-C$_{10}$H$_{21}$)(n-C$_{12}$H$_{25}$); —O—isoC$_{18}$H$_{38}$;
—O—CH$_2$—CH(n-C$_6$H$_{13}$)(n-C$_8$H$_{17}$); —O—n-C$_{18}$H$_{37}$; or
—O-2-ethylhexyl; —O—(CH$_2$)$_3$—N(C$_2$H$_5$)$_2$;

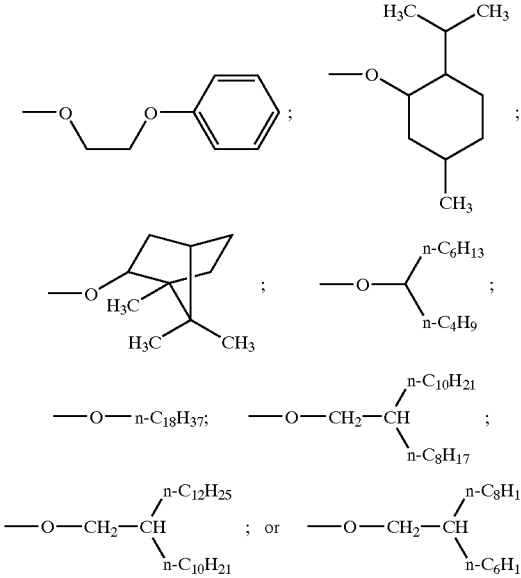

Further preferred compounds of formula (1) are those having one of the formulae

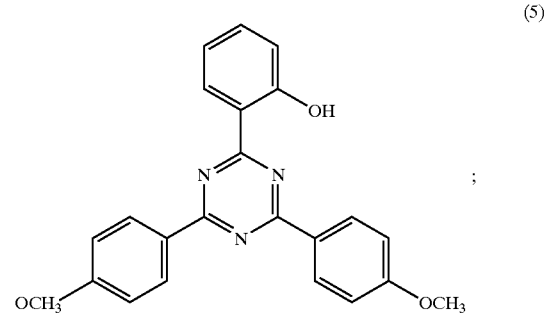
(5)

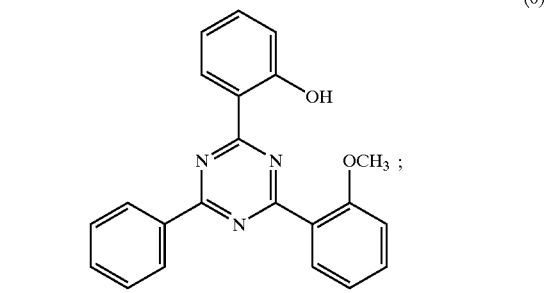
(6)

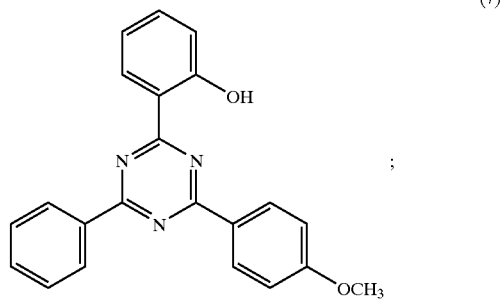
(7)

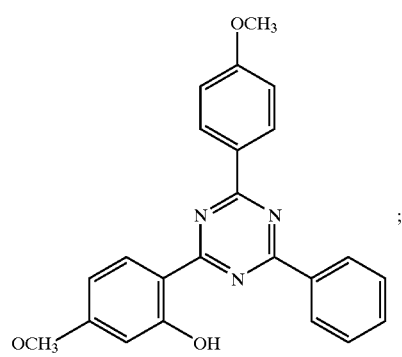
(8)
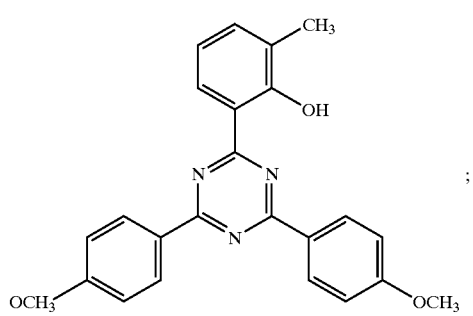
(9)
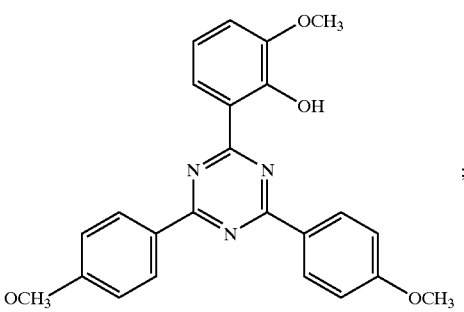
(10)
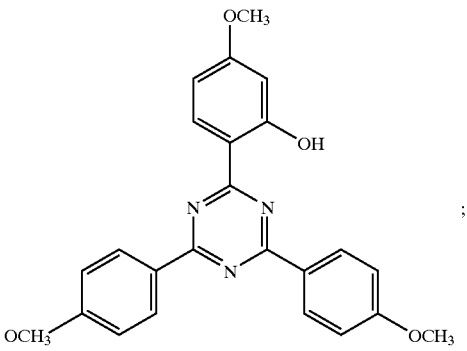
(11)
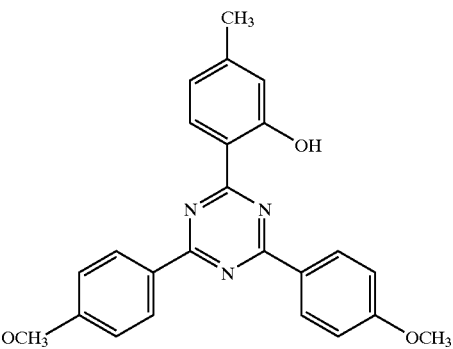
(12)
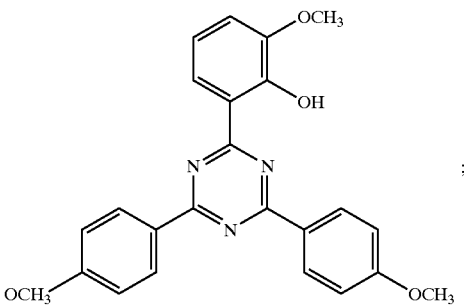
(13)
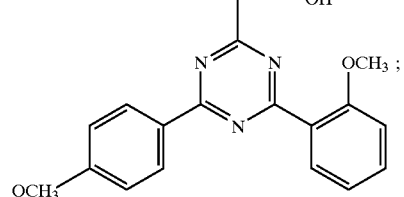
(14)
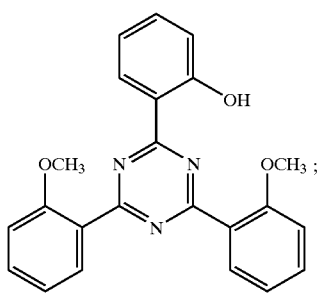
(15)
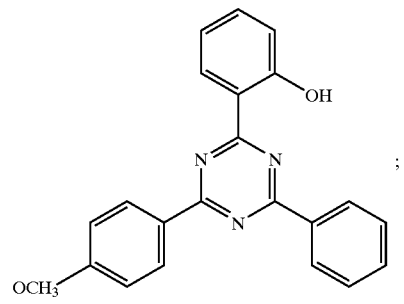
(16)

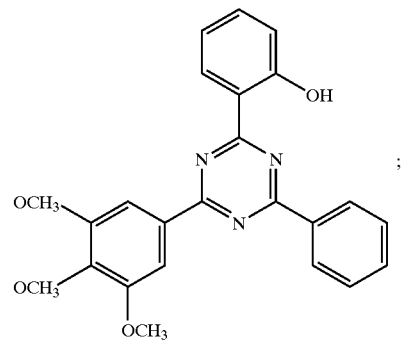 (17)
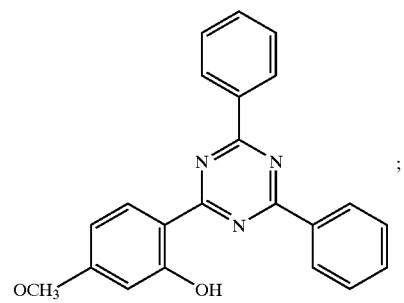 (18)
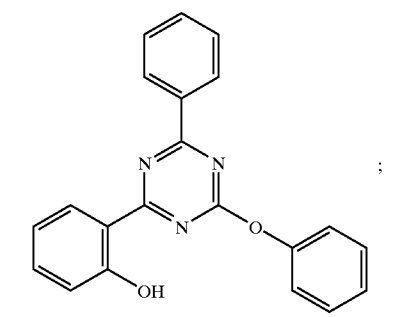 (19)
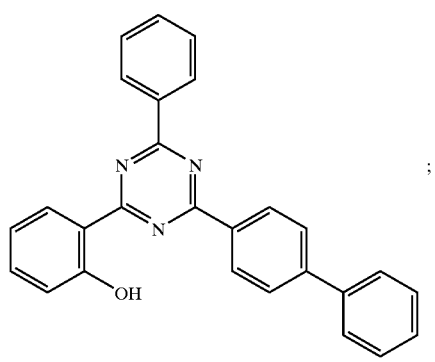 (20)
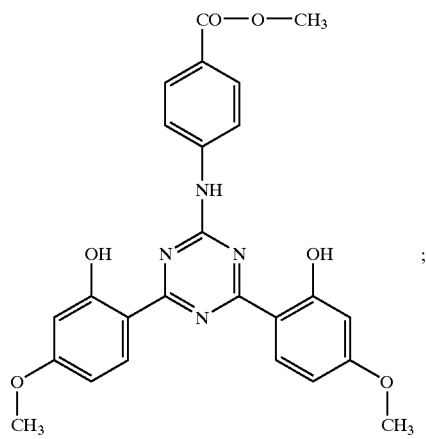 (21)
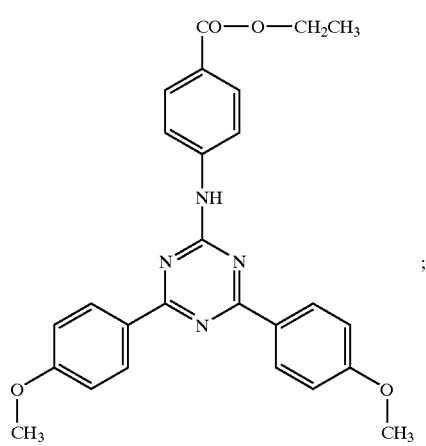 (22)
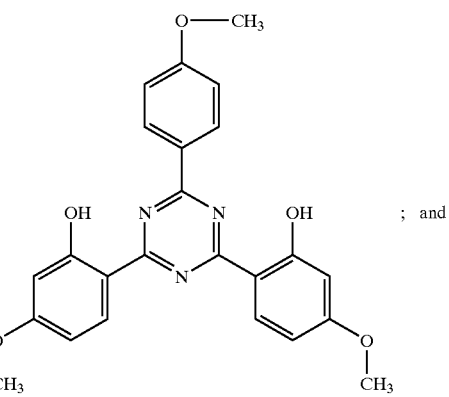 (23)
; and
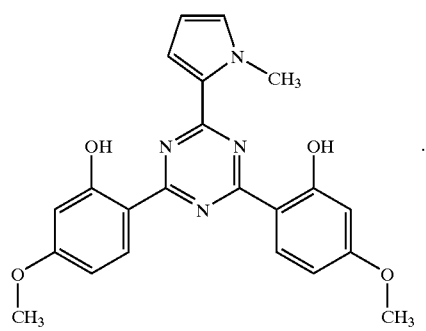 (24)

as well as 2,4,6-tris(diisobutyl-4'-aminobenzalmalonate)-s-triazine and 2,4-bis(diisobutyl-4-aminobenzalmalonate)-6-(4'-aminobenzylidenecamphor)-s-triazine.

Particularly preferred compounds of formula (1) are those having the formula:

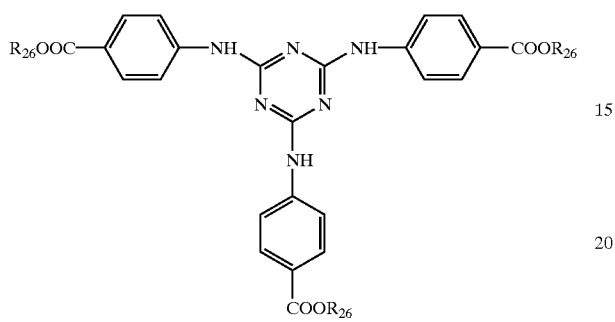

(25)

in which the individual radicals $R_{26}$ are the same or different and each is hydrogen; an alkali metal; an ammonium group $N(R_{27})_4$ in which $R_{27}$ is hydrogen or an organic radical; $C_1$–$C_3$alkyl; or a polyoxyethylene radical which contains from 1 to 10 ethylene oxide units and the terminal OH group of which may be etherified by a $C_1$–$C_3$alcohol.

In relation to the compounds of formula (25), when $R_{26}$ is an alkali metal it is preferably potassium or, especially sodium; when $R_{26}$ is a group $N(R_{27})_4$ in which $R_{27}$ has its previous significance, it is preferably a mono-, di- or tri-$C_1$–$C_4$alkylammonium salt, a mono-, di- or tri-$C_2$–$C_4$alkanolammonium salt or a $C_1$–$C_3$alkyl ester thereof; when $R_{27}$ is a $C_1$–$C_3$alkyl group, it is preferably a $C_1$–$C_2$alkyl group, more preferably a methyl group; and when $R_{27}$ is polyoxyethylene group, this preferably contains from 2–6 ethylene oxide units.

One preferred class of triazole micronised organic UV absorbers is that having the formula

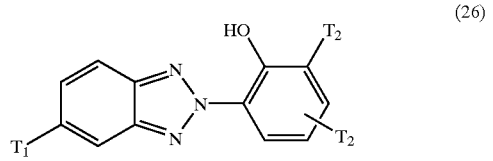

(26)

in which $T_1$ is $C_1$–$C_3$alkyl or, preferably, hydrogen; and $T_2$ is $C_1$–$C_4$alkyl, preferably t-butyl, or $C_1$–$C_4$alkyl substituted by phenyl, preferably α,α-dimethylbenzyl.

A further preferred class of triazole micronised organic UV absorbers is that having the formula

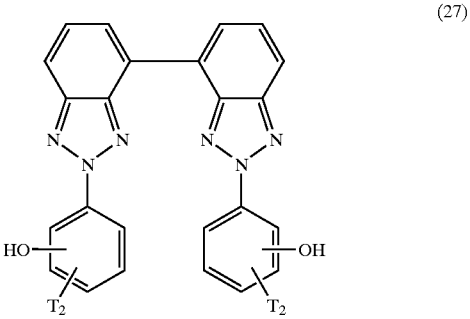

(27)

in which $T_2$ has its previous significance.

A still further preferred class of triazole micronised organic UV absorbers is that having the formula

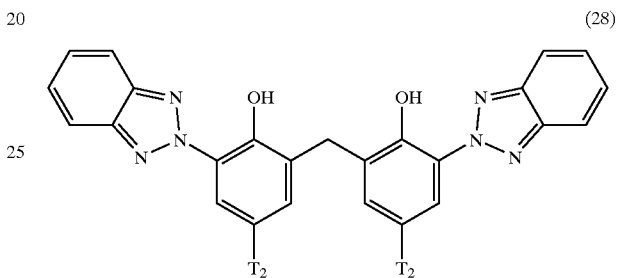

(28)

in which $T_2$ is hydrogen, $C_1$–$C_{12}$alkyl, preferably t-butyl, or $C_1$–$C_4$alkyl substituted by phenyl, preferably α,α-dimethylbenzyl.

A preferred class of vinyl group-containing amide micronised organic UV absorbers is that having the formula:

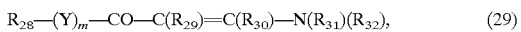

(29)

in which $R_{28}$ is $C_1$–$C_3$alkyl, preferably $C_1$–$C_2$alkyl, or phenyl optionally substituted by one, two or three substituents selected from OH, $C_1$–$C_3$alkyl, $C_1$–$C_3$alkoxy or CO—$OR_{33}$, $R_{33}$ $C_1$–$C_3$alkyl;

$R_{29}$, $R_{30}$, $R_{31}$, and $R_{32}$ are the same or different and each is $C_1$–$C_3$alkyl, preferably $C_1$–$C_2$alkyl, or hydrogen;

Y is —NH— or —O—; and m is 0 or 1.

Preferred compounds of formula (29) are 4-methyl-3-penten-2-one, ethyl-3-methylamino-2-butenoate, 3-methylamino-1-phenyl-2-buten-1-one and 3-methylamino-1-phenyl-2-buten-1-one.

A preferred class of cinnamic acid amide micronised organic UV absorbers is that having the formula:

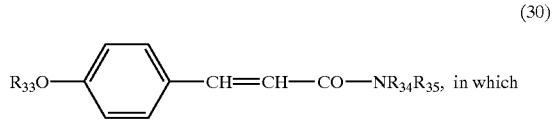

(30)

$R_{33}$ is hydroxy or $C_1$–$C_4$alkoxy, preferably methoxy or ethoxy;

$R_{34}$ is hydrogen or $C_1$–$C_4$alkyl, preferably methyl or ethyl; and $R_{35}$ is —(CONH)$_m$-phenyl in which m is 0 or 1 and the phenyl group is optionally substituted by one, two or three substituents selected from OH, $C_1$–$C_3$alkyl, $C_1$–$C_3$alkoxy or CO—OR$_4$ in which $R_4$ is $C_1$–$C_4$alkyl.

Preferably $R_{35}$ is phenyl, 4-methoxyphenyl or the phenylaminocarbonyl group.

A preferred class of sulfonated benzimidazole micronised organic UV absorbers is that having the formula

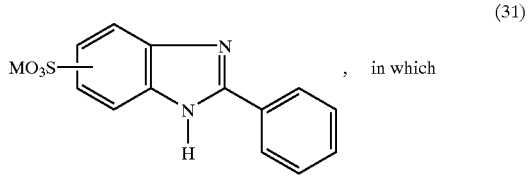
(31)
, in which

M is hydrogen or an alkali metal, preferably sodium, an alkaline earth metal, such as magnesium or calcium, or zinc.

Further preferred classes of micronised or micronisable UV absorbers used for the present invention:

p-aminobenzoic acid derivatives, typically 2-ethylhexyl-4-dimethylaminobenzoate salicylic acid derivatives, typically 2-ethylhexyl salicylate; homosalates; and isopropyl sylicylates;

benzophenone derivatives, typically 2-hydroxy-4-methoxybenzophenone;

dibenzoylmethane derivatives, typically 1-(4-tert-butylphenyl)-3-(4-methoxyphenyl)propane-1,3-dione;

diphenylacrylates, typically 2-ethylhexyl-2-cyano-3,3-diphenylacrylate and 3-(benzofuranyl)-2cyanoacrylate;

3-imidazol-4-yl-acrylic acid and 3-imidazol-4-yl-acrylate;

benzofuran derivatives, preferably 2-(p-aminophenyl) benzofuran derivatives, disclosed in EP-A-582 189, U.S. Pat. Nos. 5,338,539, 5,518,713 and EP-A613 893;

polymeric UV absorbers, such as the benzylidenemalonate derivatives described, inter alia, in EPA-709 080;

cinnamic acid derivatives, typically the 2-ethylhexyl-4methoxycinnamate or isoamylate or cinnamic acid derivatives disclosed, inter alia, in U.S. Pat. No. 5,601, 811 and WO 97/00851;

camphor derivatives, typically 3-(4'-methyl) benzylidenebornan-2-one, 3-benzylidene-bornan-2-one, N-[2(and 4)-2-oxyborn-3-ylidenemethyl)benzyl] acrylamide polymer, 3-(4'-trimethylammonium) benzylideneboman-2-one methylsulfate, 3,3'-(1,4-phenylenedime-thine)-bis(7,7-dimethyl-2-oxobicyclo-[2.2.1]heptane-1-methanesulfonic acid) and the salts thereof, 3-(4'-sulfo)benzylidenebornan-2-one and the salts thereof;

2-phenylbenzimidazole-5-sulfonic acids and the salts thereof; and menthyl-o-aminobenzoate.

In the compounds of formula (1) to (30), $C_1$–$C_{12}$ alkyl groups may be methyl, ethyl, n-propyl or isopropyl, butyl, pentyl, hexyl, heptyl, octyl, isooctyl, nonyl, decyl undecyl, dodecyl, methyl being preferred; and $C_1$–$C_3$alkoxy groups include methoxy, ethoxy, propoxy and isopropoxy, methoxy and ethoxy being preferred.

$C_2$–$C_4$ carboxyalkyl includes carboxymethyl, carboxyethyl, carboxypropyl and carboxyisopropyl, carboxymethyl being preferred.

$C_5$–$C_8$cycloalkyl includes cyclopentyl, cyclohexyl and cyclooctyl.

The compounds of formula (1) to (30) are known.

Preferably, the micronised organic UV absorber, component (a) of the new sun screen agent, has a mean particle size in the range of from 0.01 to 2, more preferably from 0.02 to 1.5, especially from 0.05 to 1.0µ.

The sun screen formulation may also comprise as optional component an oil-soluble organic UV absorber which is not micronized. This may be any known oil-soluble organic UV absorber, especially those which are already approved and marketed for cosmetic use. Such oil-soluble organic UV absorbers are described, for instance, in "Sunscreens", Development, Evaluation and Regulatory Aspects, Eds.: N. J. Lowe and N. A. Shaath, M. Dekker Inc., New York and Basel, 1990; and Ken Klein, Encyclopedia of UV absorbers for sunscreen products, Cosmetics & Toiletries 107 45–64 (1992).

The oil-soluble, non-micronised UV absorber may be, for example, a p-aminobenzoic acid derivative such as an ester, salt or an amine-modified derivative of p-aminobenzoic acid; a salicylic acid derivative such as an ester or salt thereof; a benzophenone derivative; a dibenzoylmethane derivative; a diphenylacrylate derivative; a benzofuran derivative; a polymeric UV absorber containing one or more silico-organic residues; a cinnamate ester; a camphor derivative; phenylbenzimidazole sulfonic acid and its salts; urocanic acid (3-imidazol-4-yl-acrylic acid) or its ethyl ester; or amenthyl anthranilate.

Specific examples of a p-aminobenzoic acid derivative include 4-aminobenzoic acid (PABA), ethyl dihydroxypropyl PABA having the formula

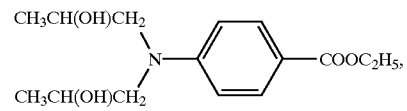

PEG-25 PABA having the formula

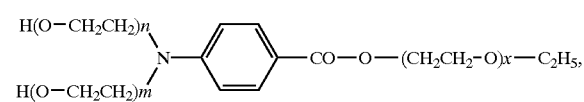

in which m, n and x are the same and each is approximately 25, octyl dimethyl PABA having the formula

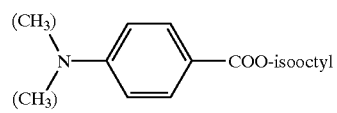

and glyceryl aminobenzoate having the formula

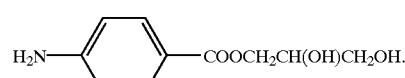

Specific examples of a salicylic acid derivative include homosalate (homomenthyl salicylate) having the formula

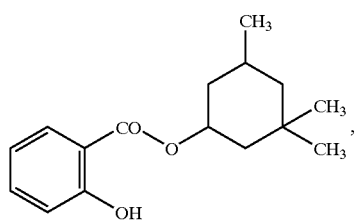

triethanolamine salicylate having the formula

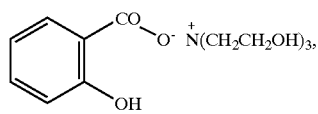

amyl p-dimethylamino benzoate having the formula

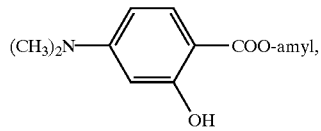

octyl salicylate having the formula

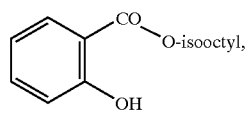

4-isopropylbenzylsalicylate having the formula

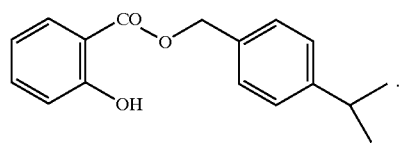

Specific examples of benzophenone derivatives include benzophenone-3-(2-hydroxy-4-methoxybenzophenone), benzophenone-4 (2-hydroxy-4-methoxybenzophenone-5-sulfonic acid) and benzophenone-8-(2,2'-dihydroxy-4-methoxybenzophenone).

A specific example of a dibenzoylmethane derivative is butyl methoxydibenzoylmethane [1-(4-tert.-butyl)-3-(4-methoxyphenyl)propane-1,3-dione].

Specific examples of a diphenylacrylate derivative include octocrylene (2-ethylhexyl-2-cyano-3,3'-diphenyl acrylate) and etocrylene (ethyl-2-cyano-3,3'-diphenyl acrylate).

Specific examples of a benzofuran derivative include the 3-(benzofuranyl)-2-cyanoacrylates described in U.S. Pat. No. 5,338,539 or EP 582189, especially the compounds having the formula

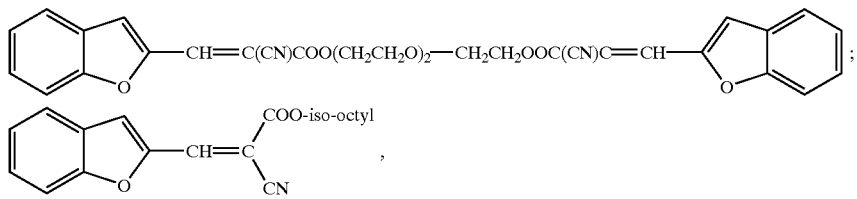

the 2-(2-benzofuranyl)-5-tert.-butylbenzoxazoles described in U.S. Pat. No. 5,518,713 and the 2-(p-aminophenyl) benzofurans described in U.S. Pat. No. 5,362,481.

Specific examples of a polymeric UV absorber containing one or more silico-organic residues are the benzylidenemalonate silicone derivatives disclosed in EP 709080, in particular the compound having the formula

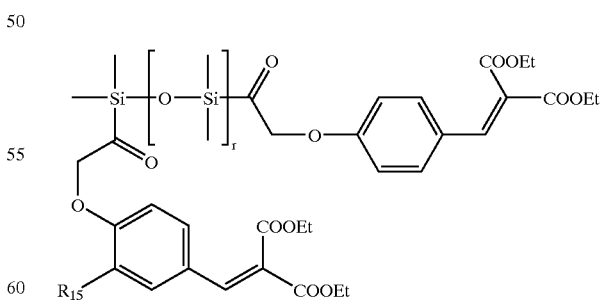

in which $R_{15}$ is H or OMe and r is approximately 7; and the polymers of the benzotriazole silicone type described in WO 94/06404, in particular the compound having the formula

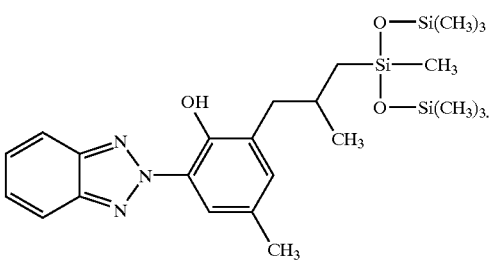

Specific examples of a cinnamate ester include octyl methoxy cinnamate (4-methoxy-cinnamic acid 2-ethylhexyl ester), diethanolamine methoxy cinnamate (diethanolamine salt of 4-methoxycinnamic acid), isoamyl p-methoxycinnamate (4-methoxycinnamic acid 2-isoamyl ester), 2,5-diisopropyl methyl cinnamate, the cinnamido derivatives disclosed in U.S. Pat. No. 5,601,811 and the derivatives described in WO 97/00851.

Specific examples of camphor derivatives are 4-methylbenzylidene camphor [3-(4'-methyl)benzylidene-bornan-2-one], 3-benzylidene camphor (3-benzylidene-bornan-2-one), polyacrylamidomethyl benzylidene camphor {N-[2 (and 4)-2-oxyborn-3-yliden-methyl)benzyl]acrylamide polymer}, trimonium benzylidene camphor sulfate [3-(4'-trimethylammonium)-benzylidene-bornan-2-one methyl sulfate], terephthalydene dicamphor sulfonic acid {3,3'-(1, 4-phenylenedimethine)-bis-(7,7-dimethyl-2-oxo-bicyclo-[2.2.1]heptan-1-methanesulfonic acid) and salts thereof and benzylidene camphor sulfonic acid [3-(4'-sulfo) benzylidene-boman-2-one] and salts thereof.

Specific examples of trianilino-s-triazine derivatives include octyl triazine [2,4,6-trianilino-(p-carbo-2'-ethyl-1'-oxy)-1,3,5-triazine, the trianilino-s-triazine derivatives disclosed in U.S. Pat. No. 5,332,568, the trianilino-s-triazine derivatives described in EP 517104, trianilino-s-triazine derivatives disclosed in EP 570838, the trianilino-s-triazine derivatives described in U.S. Pat. No. 5,252,323, the trianilino-s-triazine derivatives described in WO 93/17002-A1 and the trianilino-s-triazine derivatives disclosed in WO 97/03642-A1.

A specific example of a benzotriazole is 2-(2-hydroxy-5-methyl-phenyl)benzotriazole.

Specific examples of hydroxyphenyltriazine derivatives include, e.g. those described EP-A1-775,698, such as 2,4-bis-([4-(2-ethyl-hexyloxy)-2-hydroxy]-phenyl}-6-(4-methoxyphenyl)-1,3,5-triazine.

Specific examples of bis-resorcinol-dialkylaminotriazines are, e.g., those described in EP-A1-780,382.

The sunscreen composition of the invention may be formulated as a water-in oil or an oil-in-water dispersion, an oil or oil-alcohol lotion, a vesicular dispersion of an ionic or nonionic amphiphilic lipid, a gel, a solid stick or an aerosol formulation.

When formulated as a water-in oil or an oil-in-water dispersion, the cosmetically acceptable carrier preferably comprises 5 to 50% of an oil phase, 5 to 20% of an emulsifier and 30 to 90% of water, each by weight based on the total weight of the carrier.

The oil phase may comprise any oil conventionally used in cosmetic formulations, especially an emollient e.g., one or more of a fatty alcohol; hydrocarbon oil; a natural or synthetic triglyceride; a wax including esters of long-chain acids and alcohols as well as compounds having wax-like properties; a silicone oil; a fatty acid ester or a fatty alcohol; and lanoline-containing products.

Examples of fatty alcohols include cetyl alcohol, stearyl alcohol, octyldodecanol, cetearyl alcohol and oleyl alcohol; examples of hydrocarbon oils are, e.g., mineral oil (light or heavy), petrolatum (yellow or white), polyethylene, paraffin, squalane, microcrystalline wax, ceresin, polybutene and hydrogenated polyisobutene; examples of a natural or synthetic triglyceride include castor oil, caprylic/capric triglyceride, Japan wax, hydrogenated vegetable oil, sweet almond oil, wheat germ oil, sesame oil, hydrogenated cottonseed oil, coconut oil, wheat germ glycerides, avocado oil, corn oil, trilaurin, hydrogenated castor oil, shea butter, cocoa butter, soybean oil, mink oil, sunflower oil, safflower oil, macadamia nut oil, olive oil, hydrogenated tallow, apricot kernel oil, hazelnut oil and borage oil; examples of a wax including esters of long-chain acids and alcohols as well as compounds having wax-like properties are, e.g., carnauba wax, beeswax (white or yellow), lanolin, candelellila wax, ozokerite, lanolin oil, paraffin, Japan wax, microcrystalline wax, ceresin, jojoba oil, cetearyl esters wax, synthetic jojoba oil, synthetic beeswax and lanolin wax; a silicone oil is e.g. dimethicone or cyclomethicone; examples of a fatty acid ester or a fatty alcohol include isopropyl myristate, isopropyl palmitate, octyl palmitate, isopropyl lanolate, acetylated lanolin alcohol, the benzoate of $C_{12}$–$C_{15}$ alcohols, cetearyl octanoate, cetyl palmitate, myristyl myristate, myristyl lactate, cetyl acetate, propylene glycol dicaprylate/caprate, decyl oleate, acetylated lanolin, stearyl heptanoate, diisostearyl malate, octyl hydroxystearate, octyl hydroxystearate and isopropyl isostearate; and examples of lanoline-containing products include lanolin, lanolin oil, isopropyl lanolate, acetylated lanolin alcohol, acetylated lanolin, hydroxylated lanolin, hydrogenated lanolin and lanolin wax.

The emulsifier may comprise any emulsifier conventionally used in cosmetic formulations, e.g., one or more of an ethoxylated ester of a natural oil derivative such as a polyethoxylated ester of hydrogenated castor oil; a silicone oil emulsifier such as a silicone polyol; an optionally ethoxylated fatty acid soap; an ethoxylated fatty alcohol; an optionally ethoxylated sorbitan ester; an ethoxylated fatty acid; or an ethoxylated glyceride.

The sunscreen composition of the invention may also comprise further components which are known to perform a useful function in a sunscreen composition. Examples of such further components include, e.g., emollients, skin moisturisers, skin tanning accelerators, antioxidants, emulsion stabilisers, thickening agents such as xanthan, moisture-retention agents such as glycerine, film formers, preservatives, perfumes and colourants.

The sunscreen composition of the invention provides excellent protection of the human against the damaging effects of sunlight, while permitting safe tanning of the skin. Moreover, the sunscreen composition of the invention has a skin waterproofing effect.

The following Examples further illustrate the present invention. Parts and percentages shown therein are by weight unless otherwise stated.

EXAMPLE 1

Preparation of an O/W Sunprotection Lotion

Ingredients (% b.w.):

| | | |
|---|---|---|
| A | polyglyceryl-3 methylglucose distearate | 2.0 |
| | decyl oleate | 5.7 |
| | isopropyl palmitate | 5.0 |
| | caprylic/capric triglyceride | 6.5 |
| | octyl methoxycinnamat | 5.0 |
| B | glycerin | 3.0 |
| | phenonip | 0.5 |
| | water | 62.9 |

-continued

| C | carbomer | 0,2 |
| | isopropyl palmitate | 0,8 |
| D | 50% aqueous suspension of micronised 2,2'-methylen-bis-[6-(2H-benztriazol-2-yl)-4-(1, 1, 3,-tetramethylbutyl)-phenol (d50 = 200 nm) | 8,0 |
| E | NaOH (10%) | ad libidum |

The micronised organic UV absorber prepared by aqueous grinding (D) is added to the oil phase (A). Water is removed under vacuum so that the microparticles will transfer into the oil phase. Then, the homogenised oil phase (A) and the aqueous phase (B) are heated to 80° C. each and stirred together. Then phase (C) is added and homogenised intensively. After cooling down to room temperature under stirring the emulsion is adjusted to pH 6.5–7 with 10% NaOH-solution.

The SPF (in vitro: SPF-analyser 290) of the emulsion is 34.

If the emulsion is prepared in the manner, that the aqueous suspension of the micronised UV absorber is added as additional phase either to the aqueous phase or separately at the end of the emulsifying process the in-vitro-SPF is only 12.

EXAMPLE 2

O/W Sunprotection Lotion

Ingredients (% b.w.):

| A | polyglyceryl-3 methylglucose distearate | 2.0 |
| | decyl oleate | 5.7 |
| | isopropyl palmitate | 5.0 |
| | caprylic/capric triglyceride | 6.5 |
| | octocrylene | 2.0 |
| | octyl methoxycinnamate | 5.0 |
| B | glycerin | 3.0 |
| | terephthalidene dicampher sulfonic acid | 0.5 |
| | phenonip ® | 0.5 |
| | water | 61.5 |
| C | carbomer | 0.2 |
| | isopropyl palmitate | 0.8 |
| D | dry micronised 2,2'-methylen-bis-[6-(2H-benztriazol-2-yl)4-(1, 1, 3, 3-tetramethylbutyl)-phenol (d50 = 200 nm) | 8,0 |
| E | NaOH (10%) | ad libidum |

Dry micronised 2,2'-methylen-bis-[6-(2H-benztriazol-2-yl)-4-(1,1,3,3-tetramethylbutyl)-phenol (D) is suspended intensively in the oil phase by mixing and using supersonics. Then phase (A) and (B) are heated separately to 80° C. and mixed without stirring. After addition of (C) it is homogenised intensively and cooled down to room temperature with stirring. At the end the desired pH is adjusted with (E).

The SPF (in vitro: SPF-analyser 290) of the emulsion is 30.

EXAMPLE 3

O/W Sunprotection Lotion

Ingredients (% b.w.):

| A | polyglyceryl-3 methylglucose distearate | 2.0 |
| | decyl oleate | 5.7 |
| | isopropyl palmitate | 5.0 |
| | caprylic/capric triglyceride | 6.5 |
| | octocrylene | 2.0 |
| | octyl methoxycinnamate | 5.0 |
| B | glycerin | 3.0 |
| | phenonip ® | 0.5 |
| | water | 62.9 |
| C | carbomer | 0.2 |
| | isopropyl palmitate | 0.8 |
| D | 50% aqueous suspension of micronised 2,2'-methylen-bis-[6-(2H-benztriazol-2-yl)-4-(1, 1, 3, 3-tetramethylbutyl)-phenol (d50 = 200 nm) | 8.0 |
| E | NaOH (10%) | ad libidum |

The phases (A) and (B) are separately warmed up to 80° C. and added together without stirring. After addition of (C) the formulation is homogenised intensively. After stirring the mixture is cooled down to room temperature. Phase (D) is adjusted with citric acid to pH 5.5 and additionally stirred for 15 minutes. At the end, the desired pH is adjusted with (E).

Immediate after preparation the in-vitro-SPF of 12 is determined which will rise to SPF of 37 after three weeks of storing. The presence of the micro-particles in the oil phase is detected microscopic.

EXAMPLE 4

O/W Sunscreen Lotion

Ingredients (% b.w.):

| (A) | polyglyceryl-3-methylglucose distearate | 2.0 |
| | decyl oleate | 5.7 |
| | isopropyl palmitate | 5.0 |
| | caprylic/capric triglyceride | 6.5 |
| | 2,4-Bis{[4-(2-ethylhexyloxy)-2-hydroxy)phenyl}-6-(4-methoxyphenyl)-1, 3, 5-triazine | 2.0 |
| | octyl methoxycinnamate | 5.0 |
| (B) | glycerin | 3.0 |
| | phenonip ® | 0.5 |
| | water | 62.9 |
| C | carbomer | 0.2 |
| | isopropyl palmitate | 0.8 |
| D | 50% aqueous suspension of micronised 2,2'-methylen-bis-[6-(2H-benztriazol-2-yl)-4-(1, 1, 3, 3-tetramethylbutyl)-phenol (d50 = 200 nm) | 8.0 |
| E | NaOH (10%) | ad libidum |

2,4-Bis{[4-(2-ethylhexyloxy)-2-hydroxy]phenyl}-6(4-methoxyphenyl)-1,3,5-triazine is dissolved in octyl methoxycinnamate and added to the oil phase (A). The phases (A) and (B) are heated separately to 80° C. and added together without stirring. After addition of (C) the mixture is homogenised intensively. Under stirring the mixture is cooled down to room temperature. Phase (D) is adjusted to pH 5.5 with citric acid and added portionwise with cautious stirring. After additional stirring for ca. 15 minutes the desired pH is adjusted with (E).

Immediate after preparation the in-vitro-SPF of about 23 is determined which will rise to SPF of 54 after three weeks of storing. The presence of the micro-particles in the oil phase is detected microscopic.

EXAMPLE 5

60 g of the compound of formula

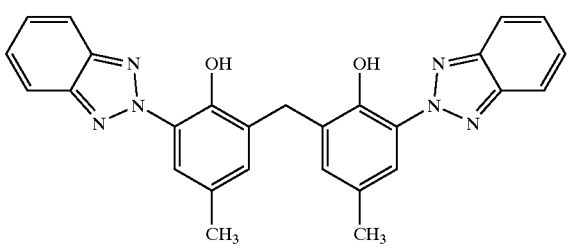
(101)

are dispersed in a solution of 12 g $C_8$–$C_{16}$alkyl-polyglucoside (Plantacare® 2000, Henkel) in 128 g of water and milled in a perl mill with 40 ml $ZrO_2$-grinding pearls to an average particle size of 170 nm.

After separating the grinding aids 0.2% xanthan gum dispersed in 0.4% 1,2-propylenglycol are added to the obtained nanodispersion (=nanodispersion 2).

This nanodispersion is further worked up to a W/O emulsion of the following composition:

20 g nanodispersion 2 (comprising 6% of the compound of formula (101))
5 g polyglyceryl-2-dipolyhydroxystearate
1 g glyceryl oleate
6 g caprylic/capric triglyceride
6 g octyldodecanol
5 g cetearyl isononanoate
1 g tocopheryl acetate
1.2 g beewax
49.3 g water
5 g glycerine
0.5 g preservative The SPF (in vitro: SPF analyser 290) is 20.2.

EXAMPLE 6

If 1.5 g 2-ethylhexyl-p-methoxycinnamate at the expense of water is added to the nano-dispersion 2 of example 5 an unexpected high SPF of 36.2 is obtained.

20 g nanodispersion 2 (comprising 6% of the compound of formula (101))
5 g polyglyceryl-2-dipolyhydroxystearate
1 g glyceryl oleate
6 g caprylic/capric triglyceride
6 g octyldodecanol
5 g cetearyl isononanoate
1 g tocopheryl acetate
1.2 g beewax
1.5 g 2-ethylhexyl-p-methoxycinnamate
47.8 g water
5 g glycerin
0.5 g preservative

What is claimed is:

1. A sun screen formulation which is formulated as a water-in oil or an oil-in-water dispersion, an oil or oil-alcohol lotion, a vesicular dispersion of an ionic or nonionic amphiphilic lipid, an oil-alcohol or alcohol gel, a solid stick or an aerosol formulation, comprising (a) a micronised organic UV absorber; and
(b) a cosmetically acceptable carrier, wherein the micronised organic UV absorber is present in an oil phase of the formulation.

2. A sun screen formulation according to claim 1 in which the micronised organic UV absorber is a triazine, a benzotriazole, a vinyl group-containing amide, a cinnamic acid amide or a sulfonated benzimidazole UV absorber.

3. A sun screen formulation according to claim 2 in which the triazine UV absorber has the formula

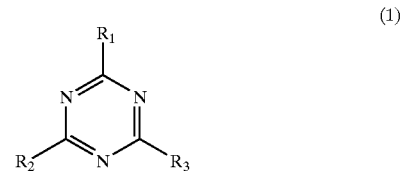
(1)

in which $R_1$, $R_2$ and $R_3$, independently, are H; OH; $C_1$–$C_3$alkoxy; $NH_2$; NH—$R_4$; $N(R_4)_2$; $OR_4$, wherein $R_4$ is $C_1$–$C_3$ alkyl; phenyl; phenoxy; anilino; pyrrolo, in which the respective phenyl, phenoxy or anilino, or pyrrolo moieties are not substituted or substituted by one, two or three substitutents selected from OH, carboxy, CO—$NH_2$, $C_1$–$C_3$alkyl, $C_1$–$C_3$alkoxy, a methylidenecamphor group, a group —(CH=CH)$_m$C(=O)—$OR_4$, a group

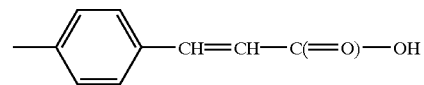

or the corresponding alkali metal, ammonium, mono-, di- or tri-$C_1$–$C_4$alkylammonium, mono-, di- or tri-$C_2$–$C_4$alkanolammonium salts, or the $C_1$–$C_3$alkyl esters thereof, a radical of formula (1a)

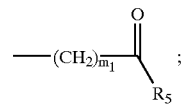

$R_5$ is hydroxy; $C_1$–$C_5$alkyl that is unsubstituted or substituted by one or more OH groups; $C_1$–$C_5$alkoxy; amino; mono- or di-$C_1$–$C_5$alkylamino; M; a radical of formula

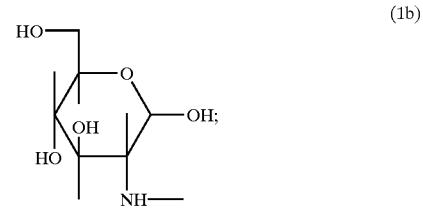
(1b)

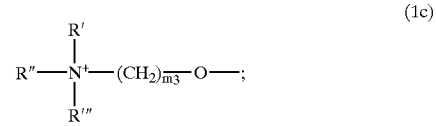
(1c)

-continued

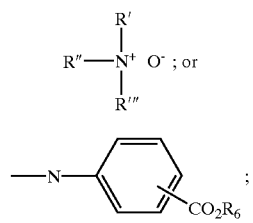 (1d)

or

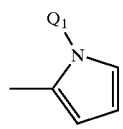 (1e)

R', R" and R'" are each independently of the others $C_1$–$C_{14}$alkyl that is unsubstituted or substituted by one or more OH groups;

$R_6$ is hydrogen; M; $C_1$–$C_5$alkyl; or a radical of the formula —$(CH_2)_{m_2}$—O—$T_1$;

M is a metal cation;

$T_1$ is hydrogen; or $C_1$–$C_8$alkyl;

m is 0 or 1;

$m_1$ is from 1 to 5;

$m_2$ is from 1 to 4;

$m_3$ is from 2 to 14.

4. A sun screen formulation according to claim 2 in which the triazine UV absorber has the formula

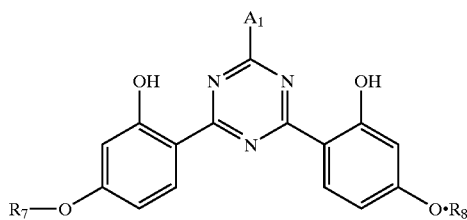 (2)

in which $R_7$ and $R_8$, independently of one another, are $C_1$–$C_{18}$alkyl; $C_2$–$C_{18}$alkenyl; a radical of the formula —$CH_2$—$CH(-OH)$—$CH_2$—O—$T_1$; or; a radical of the formula —$(CH_2)_{\overline{m_1}}$O—$((CH_2)_{\overline{m_2}}T_2$; a radical of the formula

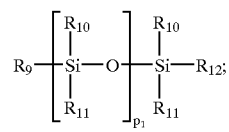 (2a)

$R_9$ is a direct bond; a straight-chain or branched $C_1$–$C_4$alkylene radical or a radical of the formula —$C_{m_1}H_{2m_1}$— or —$C_{m_1}H_{2m_1}$O—;

$R_{10}$, $R_{11}$, and $R_{12}$, independently of one another, are $C_1$–$C_{18}$alkyl; $C_1$–$C_{18}$alkoxy or a radical of the formula

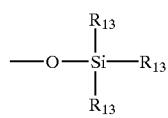

$R_{13}$ is $C_1$–$C_5$alkyl;

$T_1$ is hydrogen; or $C_1$–$C_8$alkyl;

$m_1$, $m_2$ and $m_3$, independently of one another, are 1 to 4;

$p_1$ is 0 or a number from 1 to 5;

$A_1$ is a radical of the formula

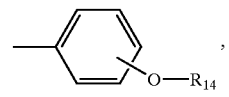 (2b)

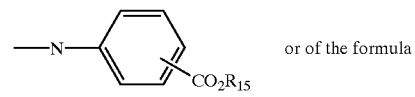 (2c)

or of the formula

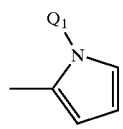 (2d)

$R_{14}$ is hydrogen; $C_1$–$C_{10}$alkyl, —$(CH_2CHR_{16}$—O$)_{n_1}$—$R_{15}$; a —$CH_2$—$CH(-OH)$—$CH_2$—O—$T_1$; or radical of the formula —$(CH_2)_{\overline{m_1}}$O—$((CH_2)_{\overline{m_2}}T_2$;

$R_{15}$ is hydrogen; M; $C_1$–$C_5$alkyl; or a radical of the formula —$(CH_2)_{m_2}$—O—$T_1$;

$R_{16}$ is hydrogen; or methyl;

$Q_1$ $C_1$–$C_{18}$alkyl;

M is a metal cation; and $n_1$ is 1–16.

5. A sun screen formulation according to claim 2 in which the triazine compound has the formula

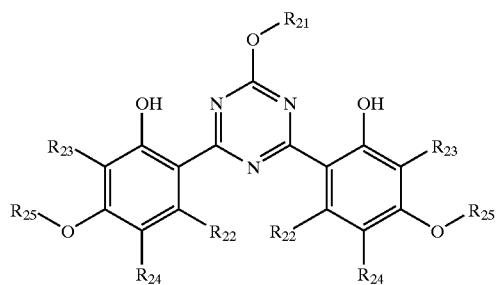 (3)

in which $R_{21}$ is $C_1$–$C_{30}$alkyl; $C_2$–$C_{30}$alkenyl; unsubstituted or $C_1$–$C_5$alkyl-mono- or polysubstituted $C_5$–$C_{12}$cycloalkyl, $C_1$–$C_5$alkoxy-$C_1$–$C_{12}$alkyl; amino-$C_1$–$C_{12}$alkyl; $C_1$–$C_5$monoalkylamino-$C_1$–$C_{12}$alkyl; $C_1$–$C_5$dialkylamino-$C_1$–$C_{12}$alkyl; a radical of the formula

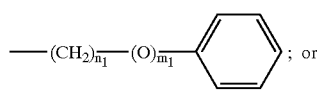 ; or (3a)

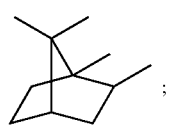 ; (3b)

$R_{22}$, $R_{23}$ and $R_{24}$, independently of one another, are hydrogen, hydroxyl, $C_1$–$C_{30}$alkyl, $C_2$–$C_{30}$alkenyl, $R_{25}$ is hydrogen; or $C_1$–$C_5$alkyl;

$m_1$ is 0 or 1; and $n_1$ is 1 to 5.

6. A sun screen formulation according to claim 5 in which the triazine compound has the formula

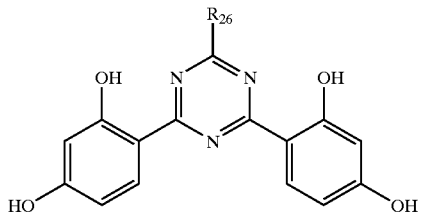
(4)

wherein $R_{26}$ is —O—CH$_2$—CH(n-C$_{10}$H$_{21}$)(n-C$_{12}$H$_{25}$); —O—isoC$_{18}$H$_{38}$;

—O—CH$_2$—CH(n-C$_6$H$_{13}$)(n-C$_8$H$_{17}$) —O—n-C$_{18}$H$_{37}$; or

—O-2-ethylhexyl; —O—(CH$_2$)$_3$—N(C$_2$H$_5$)$_2$;

[structures for menthyl and phenoxyethyl groups];

[bornyl structure]; —O—CH(n-C$_6$H$_{13}$)(n-C$_4$H$_9$);

—O—n-C$_{18}$H$_{37}$; —O—CH$_2$—CH(n-C$_{10}$H$_{21}$)(n-C$_8$H$_{17}$);

—O—CH$_2$—CH(n-C$_{12}$H$_{25}$)(n-C$_{10}$H$_{21}$); or —O—CH$_2$—CH(n-C$_8$H$_{17}$)(n-C$_6$H$_{13}$).

7. A sun screen formulation according to claim 2 in which the triazine compound has the formula

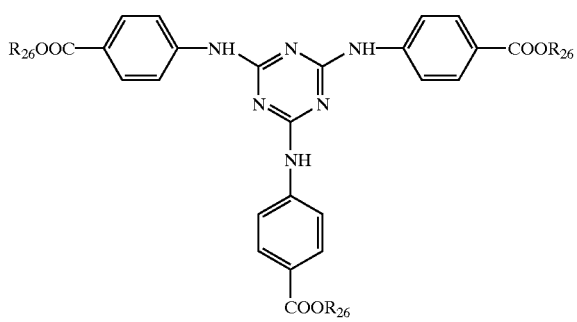
(25)

in which the individual radicals $R_{26}$ are the same or different and each is hydrogen; an alkali metal; an ammonium group $N(R_{27})_4$ in which $R_{27}$ is hydrogen or an organic radical; $C_1$–$C_3$alkyl; or a polyoxyethylene radical which contains from 1 to 10 ethylene oxide units and the terminal OH group of which may be etherified by a $C_1$–$C_3$alcohol.

8. A sun screen formulation according to claim 1 in which the triazole organic UV absorber has the formula

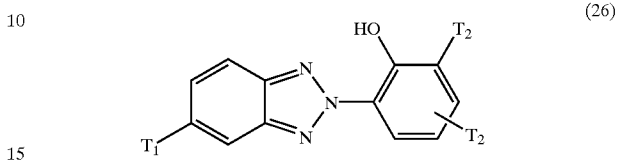
(26)

in which $T_1$ is $C_1$–$C_3$alkyl or hydrogen; and $T_2$ is $C_1$–$C_4$alkyl.

9. A sun screen formulation according to claim 1 in which the triazole organic UV absorber has the formula

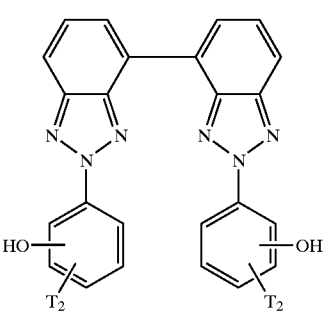
(27)

in which $T_2$ is $C_1$–$C_4$alkyl.

10. A sun screen formulation according to claim 2 in which the benzotriazole organic UV absorber has the formula

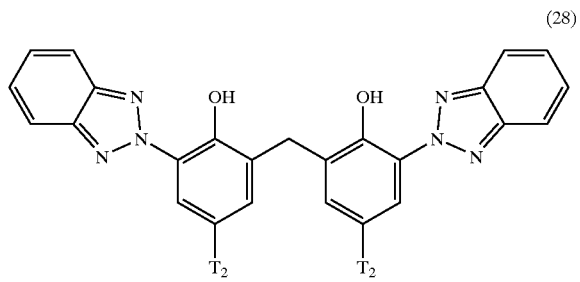
(28)

in which $T_2$ is hydrogen, $C_1$–$C_{12}$alkyl or $C_1$–$C_4$alkyl substituted by phenyl.

11. A sun screen formulation as defined in claim 10 in which $T_2$ is t-butyl.

12. A sun screen formulation according to claim 2 in which the vinyl group-containing amide organic UV absorber has the formula

$R_{28}$—(Y)$_m$—CO—C(R$_{29}$)=C(R$_{30}$)—N(R$_{31}$)(R$_{32}$),  (29)

in which $R_{28}$ is $C_1$–$C_3$alkyl, phenyl or phenyl substituted by one, two or three substituents selected from OH, $C_1$–$C_3$alkyl, $C_1$–$C_3$alkoxy or CO—OR$_{33}$, $R_{33}$ $C_1$–$C_3$alkyl;

$R_{29}$, $R_{30}$, $R_{31}$, and $R_{32}$ are the same or different and each is $C_1$–$C_3$alkyl or hydrogen;

Y is —NH— or —O—; and m is 0 or 1.

13. A sun screen formulation according to claim 2 in which the cinnamic acid amide organic UV absorber has the formula

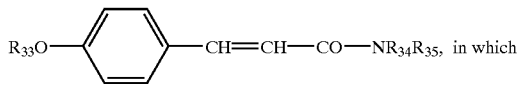
(30)

$R_{33}$ is hydroxy or $C_1$–$C_4$alkoxy, $R_{34}$ is hydrogen or $C_1$–$C_4$alkyl, and $R_{35}$ is —(CONH)$_m$-phenyl in which m is 0 or 1 and the phenyl group is optionally substituted by one, two or three substituents selected from OH, $C_1$–$C_3$alkyl, $C_1$–$C_3$alkoxy or CO—OR$_4$ in which $R_4$ is $C_1$–$C_4$alkyl.

14. A sun screen formulation according to claim 2 in which the sulfonated benzimidazole organic UV absorber has the formula:

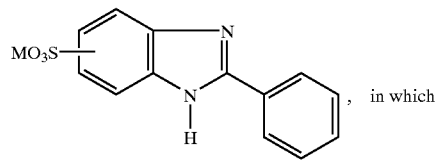
, in which

M is hydrogen or an alkali metal, an alkaline earth metal or zinc.

15. A sun screen formulation according to claim 1 in which the micronised organic UV absorber, component (a), has a mean particle size in the range of from 0.1 nm to 2μ.

16. A sun screen formulation according to claim 1 wherein the sun screen formulation additionally comprises an oil-soluble organic UV absorber selected from a p-aminobenzoic acid derivative; a salicylic acid derivative; a benzophenone derivative; a dibenzoylmethane derivative; a diphenylacrylate derivative; a benzofuran derivative; a polymeric UV absorber containing one or more silico-organic residues; a cinnamate ester; a camphor derivative; a trianilino-s-triazine derivative; phenylbenzimidazole sulfonic acid or one of its salts; urocanic acid (3-imidazol-4-yl-acrylic acid) or its ethyl ester; menthyl anthranilate; a benzotriazole; a hydroxyphenyltriazine derivative; and a bis-resorcinol-dialkylaminotriazine.

17. A sunscreen formulation according to claim 1 comprising 0.5 to 10% by weight of a micronised organic UV absorber (a); and a cosmetically acceptable carrier (b).

18. A method for the preparation of a sunscreen formulation according to claim 1, wherein an organic UV absorber is micronised in a first step, and incorporated as a powder into the oil phase of the formulation.

19. A method according to claim 18, wherein the micronised organic UV absorber is coated before incorporating with a surface active agent or a polymer.

20. A method according to claim 19, wherein the surface active agent is an anionic, cationic, nonionic or amphoteric surfactant.

21. A method for the preparation of the sunscreen formulation according to claim 1 by micronising the organic UV absorber in the first step as aqueous suspension, mixing the micronised organic UV absorber with the oil phase of the sunscreen composition in a second step and storing the formulation for at least three weeks in a final step.

22. A method for the preparation of the sunscreen formulation according to claim 1 by micronising the organic UV absorber in the first step as aqueous suspension, mixing the micronised organic UV absorber with the oil phase of the sunscreen composition in a second step and removing the water from the aqueous phase in the final step.

23. A method according to claim 22, wherein the water is removed by applying a vacuum.

* * * * *